United States Patent
Grainger et al.

(10) Patent No.: US 10,646,687 B2
(45) Date of Patent: May 12, 2020

(54) THERAPEUTIC PERCUSSIVE PILLOW

(71) Applicant: David A. Grainger, Wichita, KS (US)

(72) Inventors: David A. Grainger, Wichita, KS (US); Meagan E. Grainger, Wichita, KS (US)

(*) Notice: Subject to any disclaimer, the term of this patent is extended or adjusted under 35 U.S.C. 154(b) by 209 days.

(21) Appl. No.: 15/573,911

(22) PCT Filed: May 11, 2016

(86) PCT No.: PCT/US2016/031703
§ 371 (c)(1),
(2) Date: Nov. 14, 2017

(87) PCT Pub. No.: WO2016/186903
PCT Pub. Date: Nov. 24, 2016

(65) Prior Publication Data
US 2018/0272102 A1 Sep. 27, 2018

Related U.S. Application Data

(60) Provisional application No. 62/162,300, filed on May 15, 2015.

(51) Int. Cl.
*A61M 21/02* (2006.01)
*A47G 9/10* (2006.01)
(Continued)

(52) U.S. Cl.
CPC ............ *A61M 21/02* (2013.01); *A47G 9/007* (2013.01); *A47G 9/1009* (2013.01);
(Continued)

(58) Field of Classification Search
CPC .............. A47G 9/007; A47G 9/1045; A47G 2009/006; A47G 2009/1018; A47G 9/1036; A47G 9/1009; A61H 2201/0169; A61H 23/0254; A61H 2201/0142; A61H 2201/0149; A61H 2201/0207; A61H 2201/0228; A61H 2201/1215;
(Continued)

(56) References Cited

U.S. PATENT DOCUMENTS

| 2,859,731 A | 6/1957 | Sutton |
| 3,137,092 A | 6/1964 | Salerno |
| 2007/0074348 A1 * | 4/2007 | Carlton .................... A47D 9/02 5/639 |

FOREIGN PATENT DOCUMENTS

| CN | 204181359 U | * 3/2015 |
| CN | 204181359 U | 3/2015 |

(Continued)

OTHER PUBLICATIONS

International Search Report and Written Opinion of PCT/US2016/031703 dated Aug. 8, 2016, all enclosed pages cited.
(Continued)

*Primary Examiner* — Christine H Matthews
*Assistant Examiner* — Joshua Daryl D Lannu
(74) *Attorney, Agent, or Firm* — Burr & Forman LLP

(57) ABSTRACT

A pillow including a percussion assembly, a padding material, and a pillow cover configured to enclose the percussion assembly and the padding. The percussion assembly is configured to articulate causing the pillow padding and pillow cover to expand and contract.

12 Claims, 5 Drawing Sheets

(51) Int. Cl.
*A47G 9/00* (2006.01)
*A61H 23/00* (2006.01)
*A61H 23/02* (2006.01)
*A61M 21/00* (2006.01)

(52) U.S. Cl.
CPC ......... *A47G 9/1036* (2013.01); *A47G 9/1045* (2013.01); *A61H 23/006* (2013.01); *A61H 23/0254* (2013.01); *A47G 2009/006* (2013.01); *A47G 2009/1018* (2013.01); *A61H 2201/0134* (2013.01); *A61H 2201/0142* (2013.01); *A61H 2201/0149* (2013.01); *A61H 2201/0169* (2013.01); *A61H 2201/0207* (2013.01); *A61H 2201/0228* (2013.01); *A61H 2201/0257* (2013.01); *A61H 2201/1215* (2013.01); *A61H 2201/1418* (2013.01); *A61H 2201/5035* (2013.01); *A61H 2201/5048* (2013.01); *A61M 2021/0022* (2013.01); *A61M 2021/0027* (2013.01); *A61M 2021/0061* (2013.01); *A61M 2021/0066* (2013.01); *A61M 2205/3646* (2013.01); *A61M 2205/3653* (2013.01)

(58) Field of Classification Search
CPC .... A61H 2201/1418; A61H 2201/5035; A61H 2201/5048; A61H 23/006; A61H 2201/0134; A61H 2201/0257; A61M 2021/0061; A61M 2021/0027; A61M 2021/0022; A61M 21/02; A61M 2205/3653; A61M 2205/3646; A61M 2021/0066

See application file for complete search history.

(56) References Cited

FOREIGN PATENT DOCUMENTS

| | | |
|---|---|---|
| EP | 2025266 A1 | 2/2009 |
| JP | 2003235919 A | 8/2003 |
| WO | 2010/067978 A2 | 6/2010 |

OTHER PUBLICATIONS

Chapter I IPRP of PCT/US2016/031703 dated Nov. 21, 2017, all enclosed pages. cited.

* cited by examiner

THERAPEUTIC PERCUSSIVE PILLOW

CROSS REFERENCE TO RELATED APPLICATIONS

This application claims the benefit of U.S. Provisional Application No. 62/162,300 filed on May 15, 2015, the entire contents of which are hereby incorporated herein by reference.

TECHNOLOGICAL FIELD

An example embodiment of the present invention relates to therapeutic devices and, more particularly, to a therapeutic percussive pillow.

BACKGROUND

There are currently several pillows, cushions, and noise machines which simulate the comforting sounds, such as rain, white noise, and/or the like. These sound devices are used to enhance calm in an individual listening to the comforting sound. Some sound pillows or cushions may be equipped with a warming pack or element to provide a warm sensation to the user to further enhance a calming state.

BRIEF SUMMARY

In an example embodiment a therapeutic pillow is provided including a percussion assembly, a padding material, and a pillow cover configured to enclose the percussion assembly and the padding. The percussion assembly is configured to articulate causing the pillow padding and pillow cover to expand and contract.

In an example embodiment of the pillow, the percussion assembly includes a motor, a controller electrically connected to the motor and configured to supply a drive signal to the motor, a percussion cam configured to rotate based on a motor output, and at least one percussion plate configured to expand and contract based on the rotation of the percussion cam. In some example embodiments of the pillow, the percussion assembly also includes at least one cam rod rotatably connected to the percussion cam at a first end and in physical contact with the at least one percussion plate at a second end. The at least one cam rod translates the cam rotation to the at least one percussion plate causing the percussion plate to expand and contract.

In some example embodiments of the pillow, the percussion assembly also includes a speaker for outputting a sound based on an audio signal. The controller is further configured supply the audio signal to the speaker. In an example embodiment, the pillow also includes a warming member configured to be enclosed within the pillow cover.

In an example embodiment of the pillow, the percussion assembly also includes a user interface configured to cause the controller to adjust the drive signal. In some example embodiments, the pillow also includes a power switch configured to supply or isolate electrical power to the percussion assembly. In an example embodiment of the pillow, the percussion assembly also includes an elastic member configured to bias the at least one percussion plate toward the percussion cam. In some example embodiments of the pillow, the at least one percussion plate comprises two opposing percussion plates.

BRIEF DESCRIPTION OF THE DRAWINGS

Figure 1:
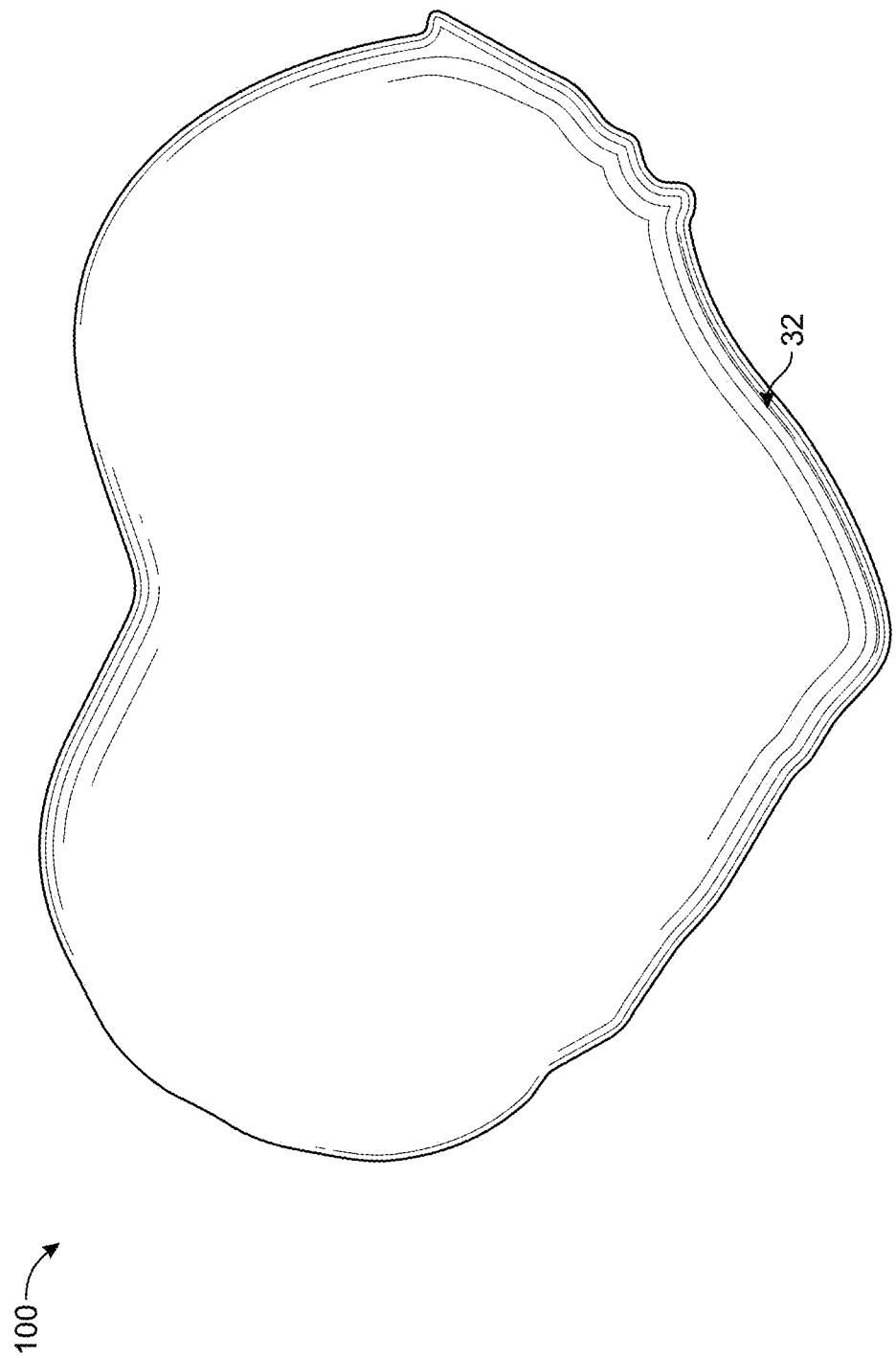
Figure 2:
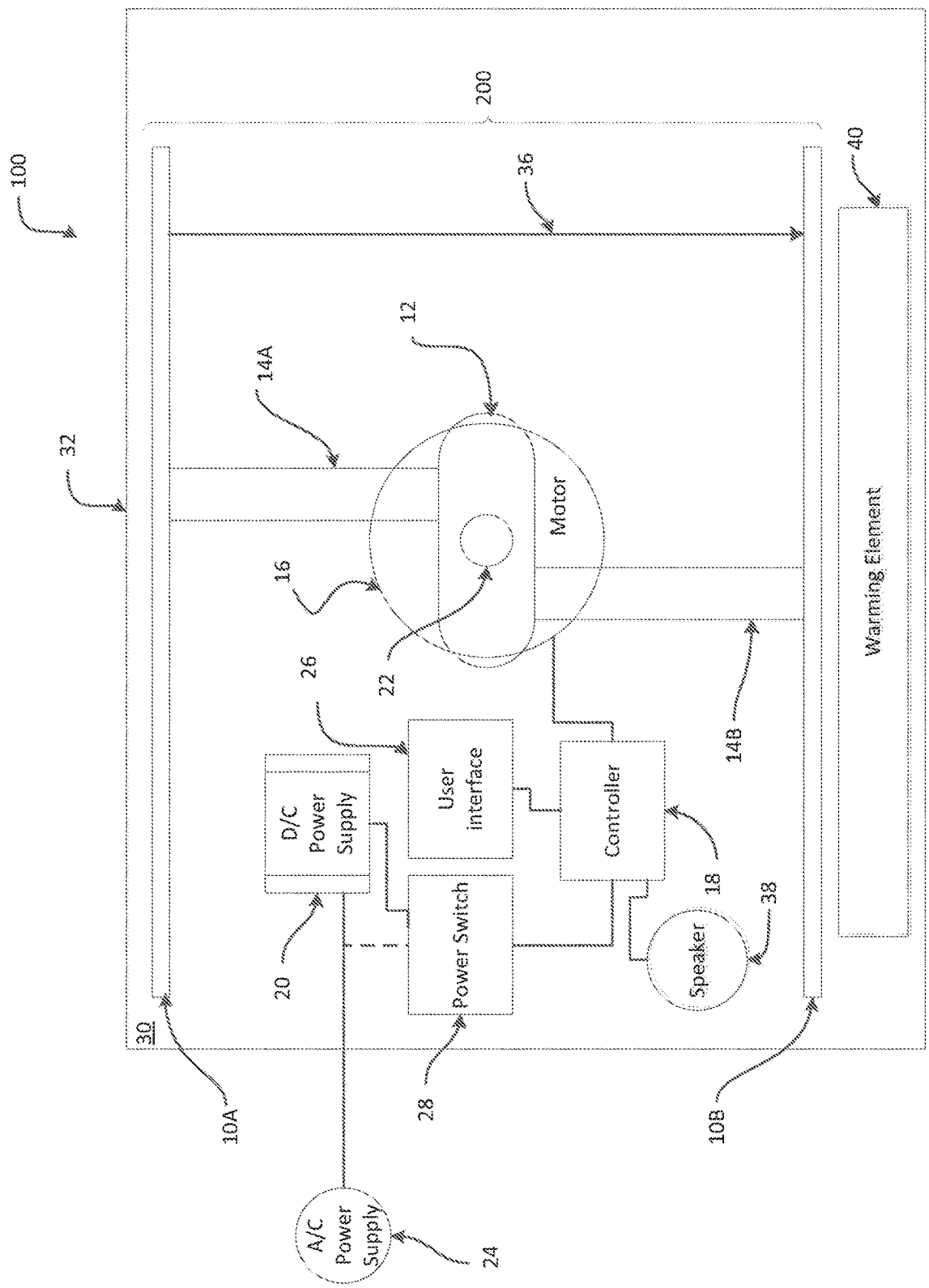
Figure 3:
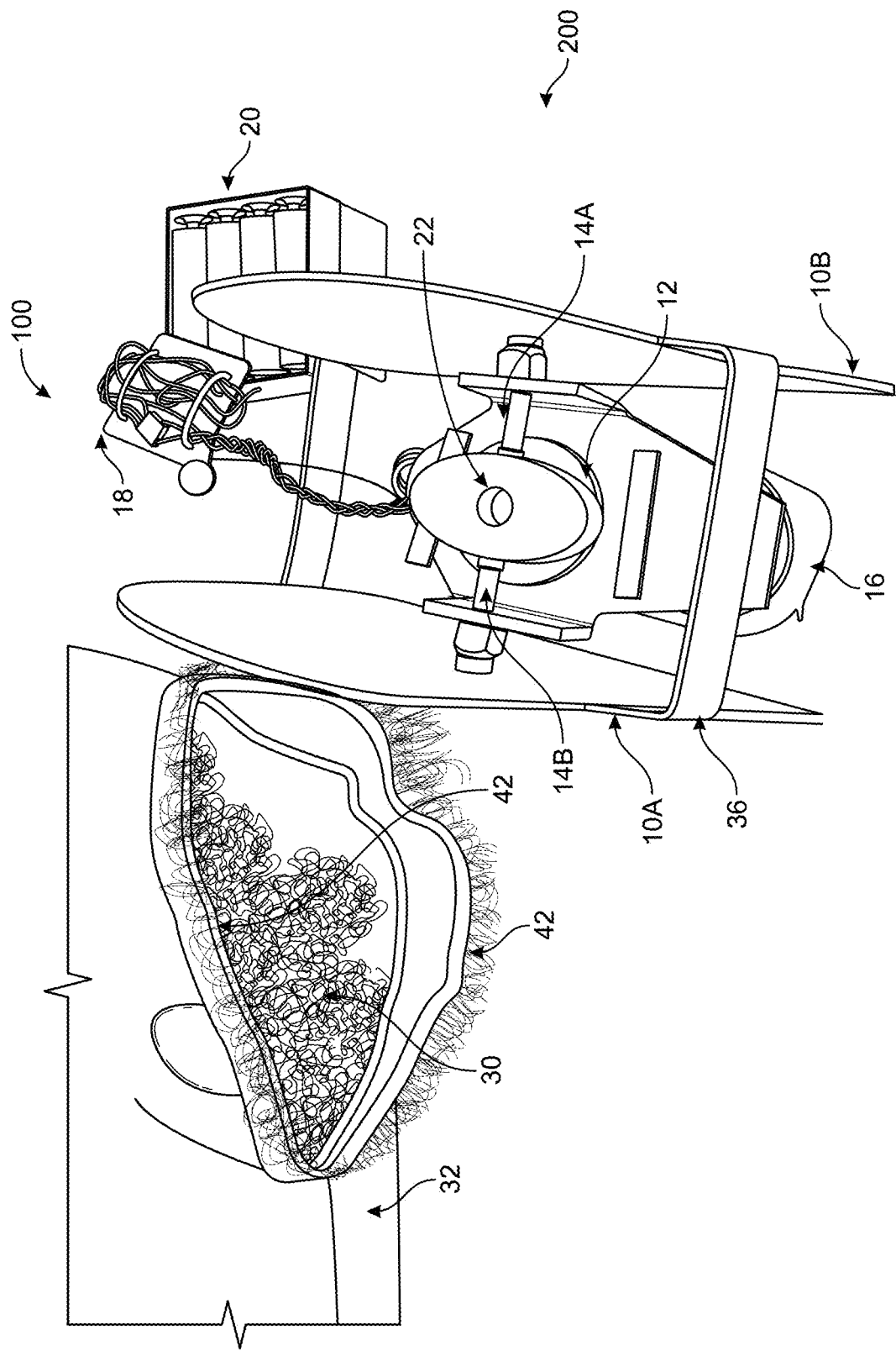
Figure 4:
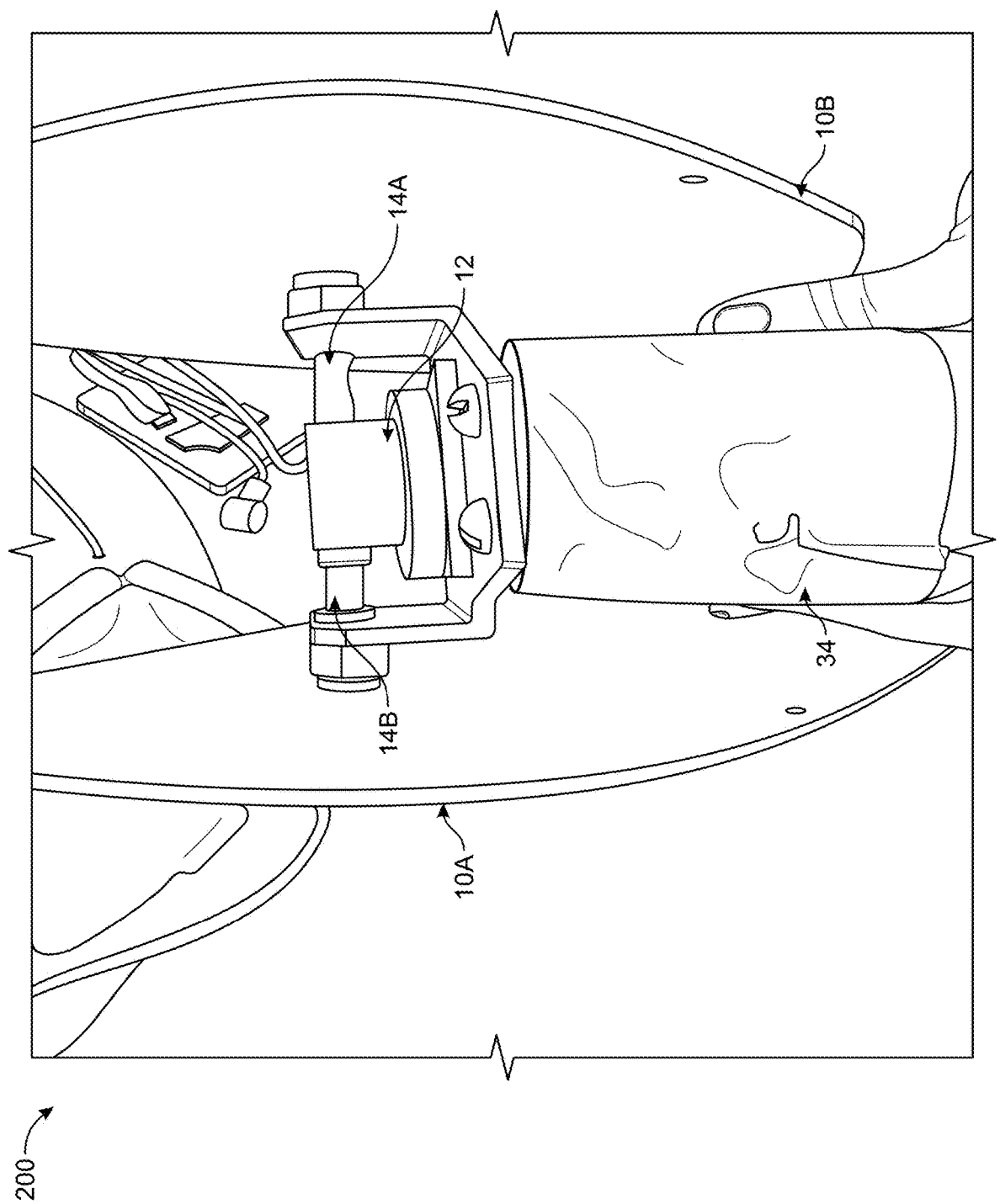
Figure 5:
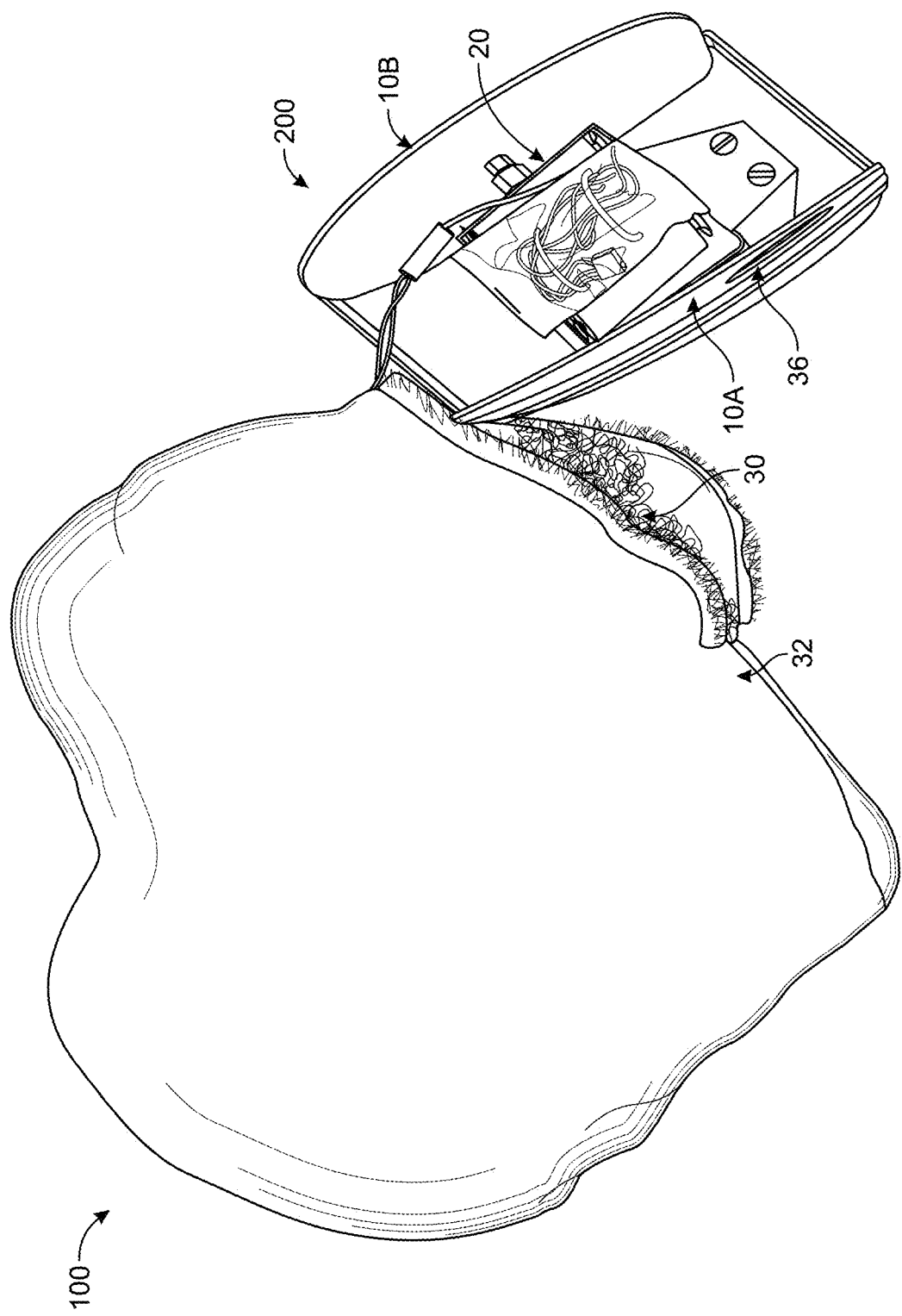

Having thus described example embodiments of the invention in general terms, reference will now be made to the accompanying drawings, which are not necessarily drawn to scale, and wherein:

FIG. 1 illustrates an example embodiment of a therapeutic pillow in accordance with an example embodiment of the present invention;

FIG. 2 is a block diagram of the therapeutic pillow in accordance with an example embodiment of the present invention;

FIGS. 3-5 illustrate example embodiments of a disassembled therapeutic pillow in accordance with an example embodiment of the present invention.

DETAILED DESCRIPTION

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

Therapeutic pillows and cushions may be configured to supply a physical output to the user to provide a claiming effect. The therapeutic pillow my pulse, throb, or percuss at a set interval to provide a soothing rhythm to the user. This percussion in some embodiments may be similar to, or simulate a heartbeat, A FIG. 1 illustrates a therapeutic pillow 100. The therapeutic pillow 100 may include a pillow cover 32 and a percussion assembly 200, discussed in FIG. 2. The pillow cover 30 may be a natural or synthetic fabric configured to enclose the percussion assembly 200. In some embodiments, the pillow cover 32 material may be a fabric, such as flannel, wool, cotton plastic sheeting, or the like. The use of soft fabric may be useful for therapeutic effect. The pillow cover 32 may be constructed in a variety of shapes and sizes, such as square, rectangle, heart, animal or the like. The pillow cover 32 may be constructed of a material in any color, although light colors such as pastels may be preferable for therapeutic effect.

In an example embodiment the therapeutic pillow 100 may be hugged of held by a user. In some embodiments, the pillow or cushion 100 may be integrated into furniture, such as, a bed, couch, chair, or the like.

FIG. 2 illustrates a block diagram of the therapeutic pillow in accordance with an example of the present invention. The therapeutic pillow 100 may include a pillow cover 32, padding 30, and a percussion assembly 200.

The padding 30 may be a natural or synthetic padding, batting, filling, or foam. The padding 30 may be configured to encompass the percussion assembly 200 on at least one side.

The percussion assembly 200 may include at least one percussion plate 10A, 10B, a percussion cam 12, cam rods 14A, 14B, a motor 16, a controller 18, and a power supply 20. In an example embodiment, the percussion assembly 200 may include two percussion plates 10A and 10B, and the percussion plates 10A and 10B may be disposed substantially parallel to each other on opposing sides of a motor assembly that may include the motor 16, the percussion cam 12 and the cam rods 14A and 14B. The percussion assembly 200 may be configured to force the percussion plates 10A and 10B apart from each other (e.g., in opposing directions substantially perpendicular to the respective planes in which the percussion plates 10A and 10B lie).

The power supply 20 may be a direct current (DC) power supply, such as batteries, rechargeable batteries, or an inverter. In some embodiments the DC power supply 20 may be electrically connected to an alternating current (AC) power supply 24, which may charge the DC power supply 20, in an embodiment in which the DC power supply includes rechargeable batteries. In some example embodiments the AC power supply 24 may supply AC electricity to the DC power supply 20 to be converted into DC electricity, such as when the DC power supply is an inverter. In a further embodiment the AC power supply 24 may directly supply the controller and or motor with electricity.

The power supply 20 may provide electricity to a controller 18, directly or through a power switch 28. The power switch 20 may operate as an electrical supply or isolation in the circuit.

The controller 18 may output a drive signal to a motor 16, such as a servo motor. The drive signal may be a continuous signal, or a series of drive pulses. The drive pulses sent by controller 18 may be at a constant interval, such as 40, or 60 pulses a minute, a staggered interval such as 2 pulses 1 second apart followed by a 2 second delay repeating, or a random interval. The controller 18 may be electrically connected to a user interface 26 configured select a drive pulse, for example the user interface may be a multi-position switch. In this example, each of the positions of the multi position switch may correspond to a predetermined drive pulse interval or pattern. In another embodiment, the user interface 26 may be a plurality of multi position switches, in which case a first switch may be configured to indicate a predetermined drive pulse intervals for each position and the second switch may be configured to indicate a predetermined drive pulse pattern for each position. In some example embodiments, the user interface 26 may be one or more variable switches, such as a dial, variable resistor, or the like. The one or more variable switches the vary the drive pulse interval and or pattern, for example increasing or decreasing the drive pulse interval speed as the variable switch is manipulated.

The motor 16 may receive the drive signal from the controller 18. The motor 16 may turn a cam shaft 22 based on the drive signal. The cam shaft 22 may be mechanically coupled to the percussion cam 12. Rotation of the cam shaft 22 may cause a rotation of the percussion cam 12. Rotation of the percussion cam 12 articulates at least one percussion plate 10A. In some example embodiments, the percussion assembly may have two opposing percussion plates 10A and 10B, rotation of the percussion cam may cause articulation of both percussion plates. In an embodiment the percussion cam 12 may rotate 360 degrees around the cam shaft 22. In some example embodiments the percussion cam rotates 90, 180, or other angular distance and cycles back to a starting position.

The percussion plates 10A, 10B may be constructed of plastic, metal wood, fiber board or the like. The percussion plates 10A, 10B may provide a surface area, such as 6 inches, 10 inches, 14 inches, or the like to transfer the articulated force to the pillow cover 32 and pillow padding 30, causing the therapeutic pillow 100 to expand and contract.

In an example embodiment, the percussion cam 12 may be mechanically coupled to one or more cam rods 14A, 14B at a first end and mechanically coupled or in physical contact with the corresponding one or more percussion plates 10A and 10B at a second end. Rotation of the percussion cam 12 may cause an extension of the cam rods 14A, 14B, which in turn articulates the percussion plates 10A, 10B. The articulation of the at least one percussion plate 10A, 10B may be an outward thrusting, percussion, throbbing, pulsing, pounding, or the like.

In some example embodiments, the percussion assembly 200 includes an elastic member 36. The elastic member 36 may be physically connected to the percussion plates 10A, 10B. The elastic member 36 may be rubber, elastic, a spring, or the like. The elastic member 36 may bias the percussion plates 10A and 10B toward the percussion cam 12 (and toward each other). In an example embodiment the elastic member 36 may be a rubber band encompassing the percussion assembly 200, as depicted in FIGS. 3 and 5.

In an example embodiment, the percussion assembly 200 may also include a speaker 38 electrically connected to the controller 18. The controller 18 may be further configured to supply an audio signal to the speaker 38. In an example embodiment, the audio output may be a comforting sound, such as, a heart beat, rain, white noise, or the like. In some example embodiments, the audio output may be configured to be synchronous or nearly synchronous the articulation of the percussion plates 10A, 10B, for example a heart beat sound synchronous with the percussion plate articulation, simulating a heart beat physically and audibly.

In some embodiments of the therapeutic pillow 100, the therapeutic pillow also includes a warming element 40. The warming element 40 may be water, grains, polymers, or the like, contained with in a flexible container, which can be heated, by a conventional oven or microwave, and retain the heat for a period of time, for example 20 minutes. Alternatively, in some embodiments, the warming element 40 could be an electrically powered heating element. The warmth may be beneficial for therapeutic effect.

FIGS. 3-5 illustrate example embodiments of a disassembled therapeutic pillow 100 in accordance with an example embodiment of the present invention. FIG. 3 depicts a percussion assembly 200, removed from the pillow cover 32, of the therapeutic pillow 100. The pillow cover 32 may have an access opening which may be closed by a retention member 42, such as snaps, toggles, Velcro, or the like. When in use the percussion assembly 200 may be embedded or surrounded by the padding 30.

The depicted percussion assembly 200 includes a controller 18 in electrical connection with the motor 16. The motor 16 includes a cam shaft 22, which is mechanically connected to the percussion cam 12. The percussion cam 12 is rotatable connected to cam rods 14A and 14B which are mechanically coupled to the percussion plates 10A, 10B. An elastic member 36, in this instance a rubber band encompasses the percussion assembly 200, biasing the percussion plates 10A, 10b toward the percussion cam 12.

FIG. 4 depicts a peripheral view of the percussion assembly 200, with the pillow cover 32 in the background. The percussion assembly 200 additionally includes an optional insulation encompassing the motor 16. The insulation 34 may be configured to absorb heat and/or sound of the motor 16.

FIG. 5 depicts the perspective bottom of the percussion assembly 200 and the pillow cover 30. The power supply 20, battery pack, in this example is affixed to the bottom of the motor 16 (not shown) between the percussion plates 10A, 10B.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A pillow comprising:
   a percussion assembly;
   a padding material; and
   a pillow cover configured to enclose the percussion assembly and the padding material, wherein the percussion assembly is configured to articulate causing the padding material and pillow cover to expand and contract,
   wherein the percussion assembly comprises:
   a motor;
   a controller electrically connected to the motor and configured to supply a drive signal to the motor;
   a percussion cam configured to rotate based on a motor output; and
   at least one percussion plate configured to expand and contract based on the rotation of the percussion cam,
   wherein the percussion assembly further comprises:
   at least one cam rod rotatably connected to the percussion cam at a first end and is in physical contact with the at least one percussion plate at a second end, and
   wherein the at least one cam rod translates the cam rotation to the at least one percussion plate causing the at least one percussion plate to expand and contract.

2. The pillow of claim 1 further comprising:
   a speaker for outputting a sound based on an audio signal, wherein the controller is further configured supply the audio signal to the speaker.

3. The pillow of claim 1 further comprising:
   a warming member configured to be enclosed within the pillow cover.

4. The pillow of claim 3, wherein the warming member is electrically powered.

5. The pillow of claim 1, wherein the percussion assembly further comprises:
   a user interface configured to cause the controller to adjust the drive signal.

6. The pillow of claim 1 further comprising:
   a power switch configured to supply or isolate electrical power to the percussion assembly.

7. The pillow of claim 1, wherein the percussion assembly further comprises:
   an elastic member configured to bias the at least one percussion plate toward the percussion cam.

8. The pillow of claim 1, wherein the at least one percussion plate comprises two opposing percussion plates.

9. The pillow of claim 1, wherein the controller is configured to provide the drive signal synchronous with an audio signal provided to a speaker.

10. The pillow of claim 1, wherein insulation is provided surrounding at least the motor to absorb motor noise.

11. A pillow comprising:
    a percussion assembly;
    a padding material; and
    a pillow cover configured to enclose the percussion assembly and the padding material, wherein the percussion assembly is configured to articulate causing the padding material and pillow cover to expand and contract,
    wherein the percussion assembly comprises:
    a motor;
    a controller electrically connected to the motor and configured to supply a drive signal to the motor;
    a percussion cam configured to rotate based on a motor output; and
    at least one percussion plate configured to expand and contract based on the rotation of the percussion cam,
    wherein the controller is configured to provide the drive signal synchronous with an audio signal provided to a speaker, and
    wherein the drive signal and the audio signal simulate a heartbeat physically and audibly.

12. A pillow comprising:
    a percussion assembly;
    a padding material;
    a pillow cover configured to enclose the percussion assembly and the padding material, wherein the percussion assembly is configured to articulate causing the padding material and pillow cover to expand and contract; and
    a warming member configured to be enclosed within the pillow cover,
    wherein the warming member is removable to enable the warming member to be heated while removed from the pillow and inserted into the pillow after being heated.

* * * * *